United States Patent [19]

Schneider et al.

[11] Patent Number: 4,598,061

[45] Date of Patent: Jul. 1, 1986

[54] CATALYST FOR THE SYNTHESIS OF METHANOL AND ALCOHOL MIXTURES CONTAINING HIGHER ALCOHOLS AND METHOD OF MAKING THE CATALYST

[75] Inventors: Michael Schneider, Ottobrunn-Riemerling; Karel Kochloefl, Moosburg; Ortwin Bock, Landshut-Kumhausen, all of Fed. Rep. of Germany

[73] Assignee: Süd-Chemie Aktiengesellschaft, Munich, Fed. Rep. of Germany

[21] Appl. No.: 694,986

[22] Filed: Jan. 25, 1985

[30] Foreign Application Priority Data

Feb. 2, 1984 [DE] Fed. Rep. of Germany ....... 3403491

[51] Int. Cl.$^4$ .......... B01J 21/04; B01J 23/06; B01J 23/10; B01J 23/72
[52] U.S. Cl. .................. 502/303; 502/302; 502/304; 502/342; 518/713
[58] Field of Search ............... 502/303, 304, 342, 302; 518/713

[56] References Cited

U.S. PATENT DOCUMENTS

| | | | |
|---|---|---|---|
| 4,107,089 | 8/1978 | Bondar et al. | 502/307 |
| 4,481,012 | 11/1984 | DiPietro et al. | 44/54 X |
| 4,513,100 | 4/1985 | Fattore et al. | 502/303 |

FOREIGN PATENT DOCUMENTS 3005551 8/1981 Fed. Rep. of Germany ...... 502/342

Primary Examiner—W. J. Shine
Attorney, Agent, or Firm—William R. Price

[57] ABSTRACT

Catalyst for the synthesis of alcohol mixtures containing methanol and higher aliphatic alcohols from CO and $H_2$, which contains, as an oxide precursor, (a) copper oxide and zinc oxide, which can be transformed into the catalytically active state by reduction with hydrogen;
(b) aluminum oxide as a thermostabilizing substance and
(c) at least one alkali carbonate or alkali oxide, the oxidic precursor comprising from 20 to 70% of the total volume of pores having a diameter between 14 and 7.5 nm, the alkali content being $13-130 \times 10^{-6}$ gram atom alkali metal per gram of the oxidic precursor, and the aluminum oxide component having been obtained from a colloidally dispersed aluminum hydroxide gel or sol.

22 Claims, No Drawings

CATALYST FOR THE SYNTHESIS OF METHANOL AND ALCOHOL MIXTURES CONTAINING HIGHER ALCOHOLS AND METHOD OF MAKING THE CATALYST

FIELD OF THE INVENTION

The invention relates to a catalyst for the synthesis of alcohol mixtures containing methanol and higher aliphatic alcohols from CO and $H_2$, which contains in the form of an oxide precursor, (a) copper oxide and zinc oxide which can be transformed into the catalytically active state by reduction with hydrogen (b) aluminum oxide as a thermostabilizing substance, and (c) at least one alkali carbonate or alkali oxide.

DESCRIPTION OF THE PRIOR ART

Such catalysts are known, for example, from German patent application No. DE-OS 30 05 551. With these catalysts, the formation of higher alcohols is enhanced by an addition of alkali oxides, in particular potassium oxide. Alcohol mixtures, consisting of methanol and higher aliphatic alcohols, in particular with propanols and butanols, can be employed as fuel alone or mixed with gasoline for driving Otto engines. If such mixtures are mixed with gasoline, no phase separation will occur, due to the presence of the higher alcohols, if accidentally a small amount of water gets into the gasoline or if the alcohol mixture contains a small amount of water.

BACKGROUND OF THE INVENTION

The mechanism by which the higher alcohols are formed along with the methanol is not yet exactly known. It is assumed that by the reaction between CO and $H_2$ —$CH_2OH$— groups are formed on the catalyst surface. These surface groups are transformed by the alkali (A) into the methylate surface groups —$CH_2OA$, to which CO is added on with formation of acetate surface groups —$CH_2CO$—$OA$. These groups are reduced with hydrogen to —$CH_2$—$CH_2OH$ surface species. These species form, on the one hand, with hydrogen ethanol, on the other hand, with alkali the ethylate surface groups —$CH_2$—$CH_2$—$OA$, which in analogy with the methylate surface groups are transformed into higher alcohols by addition of CO. Probably also aldehydes play a part in the synthesis of the higher alcohols, which would explain the formation of higher aliphatic alcohols with branched carbon chain, as for example isobutanol.

In the catalysts according to the No. DE-OS 30 05 551, the maximum yield of higher alcohols occurs at a potassium content (calculated as $K_2O$) of 1.7 wt. %. The preferred range is between 1.7 and 2.5 wt. %, the atomic ratio Cu/Zn being preferably between 0.4 and 1.9.

By the alkalization not only are new active centers created which make the synthesis of higher alcohols possible, but at the same time also the active centers for the methanol formation are blocked. The increasing alkali content in the catalyst thus results in a decreased methanol yield.

It was found, however, that the alkalization of methanol synthesis catalysts containing copper oxide and zinc oxide leads to a faster growth of the Cu crystallites and hence to a gradual deactivation. This disadvantageous effect is the more pronounced the more the methanol synthesis catalyst is alkalized.

It is the object of the invention to make available catalysts of the initially defined kind, by means of which high yields of higher alcohols can be obtained at a relatively low alkali oxide content (at which the growth of the Cu crystallites is not yet pronounced).

It has been found, surprisingly, that not only the alkalization, but also the porosity of the oxidic catalyst precursor plays a crucial role in the synthesis of higher alcohols from CO and $H_2$. It has been found that the yield of higher alcohols is generally proportional to the volume of pores with a diameter of less than about 14 nm.

SUMMARY OF THE INVENTION

The subject of the invention therefore is a catalyst of the initially defined kind which is characterized in that the oxidic precursor has a proportion of pores with a diameter between 14 and 7.5 nm of 20 to 70% of the total volume, that the alkali content is about $13-130 \times 10^{-6}$ gram atom alkali metal per gram of the oxidic precursor, and the aluminum oxide component has been obtained from an aluminum hydroxide sol or gel.

DESCRIPTION OF THE PREFERRED EMBODIMENT

It is assumed that the alkali oxides or carbonates are preferably contained in the interior of the pores. The proportion of the pores having a diameter between 14 and 7.5 nm represents 25 to 55% of the total pore volume. The mechanism by which the colloidally dispersed aluminum hydroxide affects the pore diameter is not known. The particle size of the colloidally dispersed aluminum hydroxide is not particularly critical. Colloidally dispersed aluminum hydroxides in the form of the respective sols or gels are commercially available, but can be obtained e.g. also by peptization of the freshly prepared aluminum metahydrate (Al(OH)O) with dilute nitric acid. The term "aluminum hydroxide" is to include according to the invention all hydrated forms of aluminum oxide regardless of the degree of hydration, provided the particles are present in colloidal dispersion. In general, the aluminum hydrates are expressed by the formula ($Al_2O_3 \cdot nH_2O$), where n is between about 0.1 and 3 and generally may also be higher if the adsorptively bound water molecules of the hydrate envelope are taken into consideration.

The pore diameter is determined by the method of mercury porosimetry (cf. e.g. R. Anderson, *Experimental Methods in Catalytic Research*, Academic Press, New York, 1968). According to this method, mercury is pressed onto the shaped oxidic catalyst precursor. The pressure (P) required to overcome the capillary depression in the pores of the precursor is inversely proportional to the pore diameter (d) according to the Washburn equation:

$$d = \frac{2 \text{ gamma cos THETA}_c}{P}$$

(gamma is a proportionality constant; $\text{THETA}_c$ is the contact angle of the mercury).

The catalyst of the invention is defined in the form of its oxidic precursor, as it is more appropriate to determine the pore diameter on it, because the catalyst activated by reduction is sensitive to atmospheric oxygen. The pore distribution changes insignificantly after the reduction.

Generally the catalyst of the invention has an atomic ratio Cu/Zn of 1.3 to 3.8:1, preferably 2.2 to 2.9:1. This atomic ratio is generally greater than the atomic ratio of the catalysts according to No. DE-OS 30 05 551, which is generally between 0.4 to 1.9:1. According to the invention, therefore, the share of the copper component can be increased, thereby achieving a increase in activity. Since due to the pore structure according to the invention the alkali content may be lower, the formation of copper crystallites, which at a higher atomic ratio Cu/Zn is actually supported, is reduced.

The catalyst of the invention generally contains 5 to 25 wt. %, preferably 14 to 18 wt. %, aluminum oxide (with reference to the oxidic precursor). The aluminum oxide is introduced at least for the most part in the form of the colloidally dispersed aluminum hydroxide. The aluminum oxide brings about an increased thermoresistance of the catalyst.

The catalyst of the invention contains as alkali metals preferably potassium, rubidium and/or cesium, namely in quantities of about $13-130 \times 10^{-6}$, preferably $50-100 \times 10^{-6}$ gram atom per gram of the oxidic precursor. While these quantities bring about a increased yield of higher alcohols due to the preferred pore structure of the catalyst of the invention, they are so small that changes in the physical properties of the catalyst, e.g. the above-mentioned growth of Cu crystallites and other changes of the surface structures and porosity, are much smaller than in the catalysts according to the state of the art.

As additional thermostabilizing substances besides the aluminum oxide the catalyst of the invention may contain up to 10 wt. %, preferably 3 to 7 wt. % $Ce_2O_3$ and/or $La_2O_3$ (with reference to the oxidic precursor).

The catalysts of the invention are in general obtained by precipitating the copper and zinc oxide component (a) and also optionally $Ce_2O_3$ and/or $La_2O_3$ as additional thermostabilizing substances by addition of a alkaline reacting substance from a solution of the respective salts in the presence of colloidally dispersed aluminum hydroxide. The resulting precipitate is washed and optionally calcined. Thereafter it is impregnated with compounds of the alkali metals, dried and pressed into shaped bodies in known manner.

Generally, solutions of the nitrates of Cu and Zn and also optionally of Ce and La are used and the precipitation is carried out preferably with an aqueous $K_2CO_3$ solution. The concentration of the solution is preferably 5 to 20 wt. %.

Instead of the nitrates, one can start with the respective metal formates or acetates. Alternatively, the precipitation can be carried out by means of a potassium bicarbonate solution. If the precipitation is carried out with $K_2CO_3$ or $KHCO_3$, it is not necessary to wash the precipitate very thoroughly, since in the subsequent alkalization potassium is preferably used anyway. For this reason, the precipitation may of course be carried out also with rubidium or cesium carbonate or bicarbonate. However, since a large portion of these cations is removed in washing, it is preferred to use the cheaper potassium carbonate or bicarbonate as the starting material. Also the precipitation can be carried out with sodium carbonate or sodium bicarbonate. With this method, however, the catalyst precursor must subsequently be washed out relatively thoroughly. The precipitation is possible also with ammonium carbonate or bicarbonate.

Generally, the precipitation is carried out at temperatures of 20° to 65° C. and at pH values in the range of 6.5 to 7.5. Generally, one operates at room temperature (25° C.) and at a constant pH value of $6.9 \pm 0.1$.

The precipitation can be carried out batchwise or continuously. Preferably the precipitation is carried out by continuously bringing together the solution of the nitrates of Cu and Zn and optionally also of Ce and La, containing the colloidally dispersed aluminum hydroxide, with aqueous $K_2CO_3$ solution.

Following the precipitation, the washed precipitate of the catalyst is calcined preferably at about 270° to 290° C., optionally comminuted (generally to $<1.0$ mm), and alkalized by treatment with a solution of the alkali metal compound(s), preferably under reduced pressure. For this purpose, a vessel containing the catalyst precursor may be evacuated to about 10 to 50 Torr, the solution of the alkali metal compounds being introduced into the vessel. For alkalizing the oxidic precursor, preferably the hydroxides, carbonates, hydrogen carbonates, formates and/or acetates of potassium rubidium and/or cesium are used. Generally, aqueous alcohol solutions are used for this purpose, although aqueous solutions may be used. Preferably one uses aqueous methanol or aqueous ethanol solutions.

After drying, the alkalized catalyst precursors are generally compacted in known manner into shaped bodies, for example tablets of $4.5 \times 3$ mm or $6 \times 3$ mm, lubricants such as graphite being added if desired.

Normally the oxidic catalyst precursor is activated by subjecting it to a reducing after-treatment. The latter can occur directly in the synthesis reactor and is preferably carried out by first reducing with the aid of an inert gas such as nitrogen, containing a small quantity of hydrogen. The nitrogen normally contains at first about 1.5 vol. % $H_2$. The temperature is slowly raised, for example from 100° to 235° C. over a period of 16 hours. Thereafter, the hydrogen proportion is increased, operating e.g. with 20 vol. % $H_2$ (balance $N_2$) over a period of 3 hours in the temperature range of from 235° to 270° C. The completion of the reducing treatment may occur with 99.9% $H_2$ over a period of 3 hours at 270° to 300° C. Normally, one activates at a space velocity of about 1000 to 2000 liters of reducing gas per liter of catalyst per hour.

The invention further relates to the use of the above described catalysts for the synthesis of alcohol mixtures containing methanol and higher aliphatic alcohols from CO and $H_2$. The synthesis is normally carried out at a temperature of about 250° to 320° C., preferably at 280° to 300° C., at a pressure of about 80 to 150 bar, preferably at about 100 bar, and at a space velocity of about 1000 to 10,000, preferably 3000 to 5000 liters of synthesis gas per hour and liter of catalyst, the synthesis gas containing approximately 25 to 60, preferably 30 to 50 vol. % CO, approximately 0 to 2 vol. % $CO_2$, approximately 0 to 4 vol. % $N_2$ or $CH_4$, balance $H_2$.

The production and use of the catalysts is explained by the following examples.

EXAMPLE 1 (COMPARISON EXAMPLE)

For the production of the catalyst precursor (comparison catalyst) the procedure was as follows:

As carbonate solution was used a solution of 12 wt. % $K_2CO_3$ in deionized water. For the preparation of the metal nitrate solution 626.4 g $Cu(NO_3)_2 \cdot 3H_2O$, 241.0 g $Zn(NO_3)_2 \cdot 4H_2O$ and 256.1 g $Al(NO_3)_3 \cdot 9H_2O$ was dissolved in 2 liters of deionized water and diluted to 4 liters.

The continuous precipitation occurred in a precipitator consisting of a 600 ml precipitation vessel with agitator and a collecting vessel holding 25 liters. First the precipitation vessel was filled with 400 ml deionized water, adding some metal nitrate solution and adjusting a pH value of 6.9±0.1 with carbonate solution. While stirring continuously, the simultaneous inflow of metal nitrate and carbonate solution was then regulated so that the pH value of 6.9±0.1 was maintained in the precipitation vessel. The precipitation occurred at 25° C. The precipitation time was 15 to 20 minutes.

The resulting suspension was stirred for another 30 minutes in the collecting vessel at room temperature, then suction filtered, and washed by repeated mixing with 4 liters each time of deionized water of 50° C. Thereafter, the filter cake was dried at 120° C. and calcined in a thin layer for 8 hours at 280° C. The calcined product contained 228 ppm K (determined by atomic absorption spectrometry).

200 g of the calcined and granulated (<1 mm) catalyst precursor were sprayed with a solution of 800 mg $K_2CO_3$ in 10 ml $H_2O$ and 20 ml methanol while mixing thoroughly and then exposed for 30 minutes to the vacuum of a water jet pump. The impregnated product was dried at 120° C.

After admixture with 2% natural graphite as a lubricant, the product was compacted to tablets having a diameter of 6 mm and a height of 3 mm. Table I shows the chemical, Table II the physical-mechanical data of the Catalyst 1 thus obtained.

EXAMPLE 2

Production of a Catalyst Precursor According to the Invention

A solution of 12 wt. % $K_2CO_3$ in deionized water was used as the carbonate solution. The metal nitrate solution was prepared by dissolving 1253 g $Cu(NO_3)_2 \cdot 3H_2O$ and 482 g $Zn(NO_3)_2 \cdot 4H_2O$ in 4 liters of deionized water, whereupon 696 g aluminum hydroxide sol (with 10 wt. % $Al_2O_3$) were added and diluted with deionized water to 8 liters.

The metal compounds were continuously precipitated and thereafter washed and calcined as described in Example 1.

The calcined catalyst precursor contained 260 ppm K.

200 g of the granulated (<1 mm) catalyst precursor were sprayed with a solution of 800 mg $K_2CO_3$ in 10 ml $H_2O$ and 20 ml methanol while mixing thoroughly and then exposed for 30 minutes to the vacuum of a water jet pump. Then the product was dried at 120° C.

After admixing 2% natural graphite as lubricant, the product was compacted to tablets of a diameter of 6 mm and a height of 3 mm. Table I contains the chemical, Table II the physical-mechanical data of the Catalyst 2 thus obtained.

EXAMPLE 3

Production of a Catalyst Precursor According to the Invention 200 g of the granulated catalyst precursor described in Example 2 were sprayed with a solution of 1480 mg $Rb_2CO_3$ in 10 ml $H_2O$ and 20 ml methanol while mixing thoroughly and thereafter exposed for 30 minutes to the vacuum of a water jet pump. The product was then dried at 120° C.

After admixing with 2% natural graphite, the product was compacted to tablets of a diameter of 6 mm and a height of 3 mm.

Table I contains the chemical and Table II the physical-mechanical data of Catalyst 3.

EXAMPLE 4

Production of a Catalyst Precursor According to the Invention 200 g of the granulated catalyst precursor described in Example 2 were sprayed with a solution of 2085 mg $Cs_2CO_3$ in 10 ml $H_2O$ and 20 ml methanol while mixing thoroughly and were thereafter exposed for 30 minutes to the vacuum of a water jet pump. Then the product was dried at 120° C.

After admixing 2% native graphite, the product was compacted to tablets of a diameter of 6 mm and a height of 3 mm.

Table I contains the chemical and Table II the physical-mechanical data of the Catalyst 4 thus obtained.

EXAMPLE 5

Production of a Catalyst Precursor According to the Invention

A solution of 12 wt. % $K_2CO_3$ in deionized water was used as the carbonate solution. The metal nitrate solution was prepared by dissolving 626.4 g $Cu(NO_3)_2 \cdot 3H_2O$ and 241.0 g $Zn(NO_3)_2 \cdot 4H_2O$ in 2 liters of deionized water. Thereafter, 617 g of aluminum hydroxide sol (with 10 wt. % $Al_2O_3$) were added and diluted with deionized water to 4 liters.

This material was continuously precipitated and thereafter washed and then calcined as described in analogy in Example 1.

The calcined catalyst precursor contained 315 ppm K.

200 g of the catalyst precursor were sprayed with a solution of 1300 mg $K_2CO_3$ in 30 ml $H_2O$ while mixing thoroughly and thereafter exposed for 30 minutes to the vacuum of a water jet pump. Then the product was dried at 120° C. After admixing with 2% natural graphite, the product was compacted to tablets having a diameter of 6 mm and a height of 3 mm.

Table I contains the chemical and Table II the physical-mechanical data of Catalyst 5.

EXAMPLE 6

Production of a Catalyst Precursor According to the Invention

A solution of 12 wt. % $K_2CO_3$ in deionized water was used as the carbonate solution. The metal nitrate solution was prepared by dissolving 626.4 g $Cu(NO_3)_2 \cdot 3H_2O$, 241.0 g $Zn(NO_3)_2 \cdot 4H_2O$, 31.8 g $Ce(NO_3)_2 \cdot 6H_2O$ and 31.9 g $La(NO_3)_3 \cdot 6H_2O$ in 2 liters of deionized water. Thereafter, 377 g aluminum hydroxide sol (with 10 wt. % $Al_2O_3$) were added and diluted to 4 liters.

This material was continuously precipitated and then washed and calcined as in Example 1.

The calcined catalyst precursor contained 280 ppm K.

200 g of the catalyst precursor were sprayed with a solution of 800 mg $K_2CO_3$ in 10 ml $H_2O$ and 20 ml ethanol while mixing thoroughly and then exposed for 30 minutes to the vacuum of a water jet pump. Then the product was dried at 120° C. After admixing with natural graphite, the product was compacted to tablets of a diameter of 6 mm and a height of 3 mm.

Table I contains the chemical and Table II the physical-mechanical data of the Catalyst 6 thus obtained.

EXAMPLE 7 (Catalyst Application)

Portions of 30 cc of the catalyst precursors produced according to Examples 1 to 6 were activated in a reactor (Autoclave Engineers, Erie, USA), with an internal gas circulation, with a gas consisting of 1.5 vol. % $H_2$, balance $N_2$, over a period of 16 hours from 100° to 235° C. Thereafter, the activation was continued with 20 vol. % $H_2$ (balance $N_2$) over a period of 3 hours from 235° to 270° C., and was completed over a period of 3 hours with 99.9% $H_2$ at 270° to 300° C. Subsequently, synthesis gas No. 1 or No. 2

|  | SG-1 | SG-2 |
|---|---|---|
| CO (vol. %) | 29.0 | 50.0 |
| $CO_2$ (vol. %) | 0.5 | 1.0 |
| $H_2$ (vol. %) | balance | balance | was supplied to the reactor through a mass flowmeter, a pressure of 100 bar and a space velocity of 4000 liters SG/hr and liter of catalyst being adjusted. After passage through a water cooler (10° C.), the reaction products were separated into liquids and gases. The liquid reaction products were drained at periodic intervals of 8 hours, weighed, and analyzed by gas-liquid chromatography and evaluated quantitatively by means of an electronic integrator. The gaseous reaction products wer measured after continuous depressurization by means of a gasometer and analyzed by gas chromatography. The quantitative evaluation was carried out again by means of an electronic integrator. The test results for catalysts 1 to 6 are compiled in Table III.

TABLE I

| Catalyst | Loss on Ignition 600° C. (%) | CuO (%) | ZnO (%) | $Al_2O_3$ (%) | $CeO_2$ (%) | $La_2O_3$ (%) | K ppm | Rb ppm | Cs ppm |
|---|---|---|---|---|---|---|---|---|---|
| 1 | 13.5 | 56.4 | 20.5 | 9.5 | — | — | 2490 | — | — |
| 2 | 14.9 | 55.4 | 20.2 | 9.4 | — | — | 2520 | — | — |
| 3 | 14.8 | 55.4 | 20.2 | 9.4 | — | — | 262 | 5475 | — |
| 4 | 14.8 | 55.4 | 20.2 | 9.4 | — | — | 260 | — | 8505 |
| 5 | 12.7 | 52.5 | 19.1 | 15.7 | — | — | 3995 | — | — |
| 6 | 14.0 | 51.6 | 18.8 | 9.4 | 3.1 | 3.0 | 2540 | — | — |

TABLE II

| Catalyst | BD (g/100 ml) | CS (kg/tabl.) | SA ($m^2$/g) | PV (ml/g) | Pore Distribution (%) 15000–1750 (nm) | 1750–80 (nm) | 80–14 (nm) | 14–7.5 (nm) |
|---|---|---|---|---|---|---|---|---|
| 1 | 88.4 | 12.9 (10.5–15.9) | 98 | 0.41 | 0.5 | 13.6 | 75.3 | 11.1 |
| 2 | 93.0 | 13.7 (11.0–15.9) | 130 | 0.29 | 0.8 | 1.6 | 55.6 | 42.0 |
| 3 | 92.5 | 13.2 (10.1–14.8) | 129 | 0.29 | 0.2 | 0.9 | 55.4 | 43.5 |
| 4 | 93.0 | 13.4 (10.9–15.1) | 131 | 0.28 | 0.1 | 1.5 | 54.4 | 44.0 |
| 5 | 85.0 | 13.4 (12.5–14.5) | 130 | 0.45 | 0.2 | 2.3 | 47.5 | 50.0 |
| 6 | 86.4 | 13.8 (10.0–15.2) | 109 | 0.39 | 0.5 | 1.0 | 63.2 | 36.0 |

Remarks:
BD = bulk density;
CS = crush strength;
SA = Spec. surface (after BET);
PV = Pore volume

TABLE III

Results of the Synthesis of Mixtures Consisting of Methanol and Higher Aliphatic Alcohols
T = 300° C., P = 100 bar synthesis gas, space velocity 400 liters SG per hour and liter catalyst.
Synthesis gas No. 1: CO 29.0%, $CO_2$ 0.5%, $H_2$ balance
Synthesis gas No. 2: CO 49%, $CO_2$ 1.0%, $H_2$ balance

| Catalyst No. | 1 | 2 | 2 | 3 | 4 | 4 | 5 | 6 |
|---|---|---|---|---|---|---|---|---|
| Synthesis Gas No. | 1 | 1 | 2 | 1 | 1 | 2 | 1 | 1 |
| CO Conversion % | 49.2 | 59.0 | 31.3 | 58.5 | 56.1 | 29.6 | 57.2 | 56.1 |
| Yield of Liquid Reaction Products (g/hr · 1 of cat.) | 762 | 895 | 770 | 875 | 860 | 710 | 840 | 833 |
| Composition (%) | | | | | | | | |
| Methanol | 93.4 | 92.0 | 86.1 | 91.0 | 90.0 | 83.5 | 90.0 | 91.7 |
| Higher Alcohols | 4.1 | 5.4 | 9.3 | 6.4 | 7.0 | 11.2 | 6.2 | 5.7 |
| $H_2O$ | 1.4 | 1.5 | 2.6 | 1.6 | 1.8 | 3.1 | 1.8 | 1.1 |
| By-Products | 1.1 | 1.1 | 2.0 | 1.0 | 1.2 | 2.2 | 2.0 | 1.5 |
| Yield of Higher Alcohols (g/hr · 1 of cat.) | 31.2 | 48.3 | 71.6 | 56.0 | 60.2 | 79.5 | 52.1 | 47.5 |

TABLE III-continued

Results of the Synthesis of Mixtures Consisting of Methanol and Higher Aliphatic Alcohols
T = 300° C., P = 100 bar synthesis gas, space velocity 400 liters SG per hour and liter catalyst.
Synthesis gas No. 1: CO 29.0%, $CO_2$ 0.5%, $H_2$ balance
Synthesis gas No. 2: CO 49%, $CO_2$ 1.0%, $H_2$ balance

| Catalyst No. | 1 | 2 | 2 | 3 | 4 | 4 | 5 | 6 |
|---|---|---|---|---|---|---|---|---|
| Composition of the Higher Alcohols (%) | | | | | | | | |
| $C_2H_5OH$ | 35.4 | 31.6 | 27.3 | 26.3 | 23.0 | 19.9 | 21.1 | 33.0 |
| $C_3H_7OH$ | 20.2 | 20.9 | 18.9 | 19.1 | 16.7 | 15.8 | 17.5 | 21.2 |
| $C_4H_9OH$ | 20.3 | 21.5 | 22.1 | 27.7 | 29.2 | 30.5 | 31.8 | 22.2 |
| $C_5H_{11}OH$ | 10.1 | 10.4 | 9.5 | 11.9 | 13.4 | 12.2 | 12.5 | 9.6 |
| >$C_5H_{11}OH$ + Other Org. Compounds | 14.0 | 15.6 | 22.2 | 15.0 | 17.7 | 21.6 | 17.1 | 14.0 |

We claim:

1. A catalyst, active in the reduced state for the synthesis of alcohol mixtures containing methanol and higher aliphatic alcohols from CO and $H_2$, and obtained from a metallic oxide catalyst precursor mixture which comprises
    A. copper oxide and zinc oxide, transformable upon reduction into a catalytically-active state;
    B. aluminum oxide, derived from a colloidally-dispersed aluminum hydroxide sol or gel;
    C. an alkali metal compound in which the alkali content is about $13-130 \times 10^{-6}$ gram atoms of alkali metal per gram of metallic oxide precursor mixture; and
    D. in which the pores of said metallic oxide precursor mixture, having a diameter in the range of from about 7.5–14 nm constitute about 20–70% of the total volume of pores of said metallic oxide precursor.

2. A catalyst, as defined in claim 1, in which the percentage of pores having a diameter in the range of 14–7.5 nm is between 25–55% of the total pore volume.

3. A catalyst, as defined in claim 1, in which the atomic ratio of copper:zinc is between 1.3–3.8:1.

4. A catalyst, as defined in claim 3, in which the atomic ratio of copper:zinc is between 2.2–2.9:1.

5. A catalyst, as defined in claim 1, in which the percentage of aluminum oxide is present in a concentration of 5–25% by weight, based on the weight of the metallic oxide precursor mixture.

6. A catalyst, as defined in claim 1, in which the alkali metal compound is derived from one of the alkali metals taken from Periods 4–6 of Group 1A of the Periodic Table.

7. A catalyst, as defined in claim 1, in which the concentration of the alkali metal compound is in the range of $50-100 \times 10^{-6}$ gram atoms of alkali metal per gram of metallic oxide precursor.

8. A catalyst, as defined in claim 1, in which the precursor mixture includes rare earth metal oxides of lanthanum or of the lanthanoide series.

9. A catalyst, as defined in claim 8, in which the rare earth metal oxides are present in a concentration of up to 10 wt. %, based on the weight of the metallic oxide precursor.

10. A method of preparing a catalyst precursor, as defined in claim 1, which comprises the steps of:
    A. adding an alkaline precipitating agent to a solution of the metallic salts;
    B. precipitating the metallic salts in the presence of an aluminum hydroxide sol or gel;
    C. impregnating the precipitate with a solution of an alkali metal compound;
    D. drying and calcining the precipitate; and
    E. forminig the calcined precipitate into shaped bodies.

11. A method of preparing a catalyst precursor, as defined in claim 10, in which the solution of metallic salts includes the nitrates of copper and zinc.

12. A method of preparing a catalyst precursor, as defined in claim 10, in which the alkaline precipitating agent is $K_2CO_3$ in a concentration of between about 5–20% by weight.

13. A method of preparing a catalyst precursor, as defined in claim 10, in which the step of precipitating is carried out at a pH in the range of between 6.5–7.5.

14. A method of preparing a catalyst precursor, as defined in claim 10, in which the step of precipitating the salts is at a temperature in the range of from 20°–65° C.

15. A method of preparing a catalyst precursor, as defined in claim 10, in which the step of precipitating the metal salts includes flowing the metal salt solution and the alkaline precipitating agent as separate streams together into a precipitating vessel under controlled conditions of flow, temperature and pH.

16. A method of preparing a catalyst precursor, as defined in claim 15, in which the aluminum hydroxide sol or gel is included with the metal salt solution.

17. A method of preparing a catalyst precursor, as defined in claim 15, in which a lanthanum salt is included with the metal salt solution.

18. A method of preparing a catalyst precursor, as defined in claim 15, in which a rare earth metal salt of the lanthanoide series is included with the metal salt solution.

19. A method of preparing a catalyst precursor, as defined in claim 10, in which the calcining step is carried out at a temperature in the range of from about 270°–290° C.

20. A method of preparing a catalyst precursor, as defined in claim 10, in which the calcined precipitate is impregnated with a solution of an alkali metal compound under reduced pressure.

21. A method of preparing a catalyst precursor, as defined in claim 10, in which the calcined precipitate is impregnated with an aqueous alcohol solution of an alkali metal compound.

22. A method of preparing a catalyst precursor, as defined in claim 20, in which the alkali metal compound is a hydroxide, carbonate, bicarbonate, acetate or formate of potassium, cesium or rubidium.

* * * * *